United States Patent [19]

Berglund et al.

[11] Patent Number: 5,462,878
[45] Date of Patent: Oct. 31, 1995

[54] METHOD FOR DETERMINING HYDROXY AROMATIC COMPOUNDS

[75] Inventors: Kris A. Berglund, Okemos; Joel I. Dulebohn; Beatrice A. Torgerson, both of Lansing, all of Mich.

[73] Assignee: Board of Trustees operating Michigan State University, East Lansing, Mich.

[21] Appl. No.: 301,652

[22] Filed: Sep. 6, 1994

[51] Int. Cl.⁶ .................................................. G01N 33/00
[52] U.S. Cl. .................... 436/131; 436/140; 436/164
[58] Field of Search ........................... 436/131, 140, 436/164; 422/55–58

[56] References Cited

U.S. PATENT DOCUMENTS

| | | |
|---|---|---|
| 2,621,193 | 12/1952 | Langkammerer . |
| 2,621,194 | 12/1952 | Balthis . |
| 2,621,195 | 12/1952 | Haslam . |
| 4,043,820 | 8/1977 | Landau . |
| 4,275,031 | 6/1981 | Fischer et al. ............................. 422/57 |
| 4,436,823 | 3/1984 | Blumcke et al. ........................ 436/169 |
| 5,244,811 | 9/1993 | Matthews ................................ 436/146 |
| 5,308,495 | 5/1994 | Avnir et al. ............................. 210/656 |

OTHER PUBLICATIONS

Chem. Abstracts CA 89:36135 Eskin et al., J. Chromatogr. 150(1), pp. 293–294 (1978).
Chem Abstracts CA 93:230325 Korenman et al. Zh. Prikl. Khim. (Leningrad) 53(9) p. 2154 (1980).
Chem Abstracts CA 90:47988 Nazarenko et al. Zh. Anal. Khim. 33(9) pp. 1860–1861 (1978).
Sanchez, C., et al., J. Non–Cryst. Solids 100, 65 (1988).
Sanchez, C., et al., New J. Chem. 14, 513 (1990).
Sanchez, C., et al., in "Ultrastructure Processing of Advance Ceramics", Mackenzie, J. D., Ulrich, D. R. Eds., Wiley, New York, p. 77 (1988).
Doeuff, S., et al., J. Non–Cryst. Solids 89, 206 (1987).
Gagliardi, C. D., et al., Mat. Res. Soc. Symp. Proc., 155, 127 (1989).
Livage, J., Mat. Res. Soc. Symp. Proc. 73, 717 (1986).
Gagliardi, C. D., et al., Mat. Res. Soc. Symp. Proc., 180, 801 (1990).
Watenpaugh, K., et al., Inorg. Chem. 5, 1782 (1966).
Svetich, G. W., et al., J. Am. Chem. Soc. Chem. Commun., 676 (1971).
Svetich, G. W., et al., Acata Cryst. B28, 1760 (1972).
Malhotra, K. C., et al., J. Organomet. Chem. 239, 159 (1982).
Varma, I. D., et al., J. Indian., Chem. Soc., 38, 147 (1961).

*Primary Examiner*—James C. Housel
*Assistant Examiner*—Jan M. Ludlow
*Attorney, Agent, or Firm*—Ian C. McLeod

[57] ABSTRACT

A method and test kit for the detection of hydroxy substituted aromatic compounds using a titanium film (12, 23) which reacts with the compound to change the light absorbance. Preferred films are prepared by reaction of a titanium alkoxide with an aliphatic carboxylic acid. The change in light absorbance of the film is preferably detected with an ultraviolet-visible spectrophotometer. Preferably the film is provided on a transparent slide (22) or on an inside wall of a spectrophotometer cell (10). The cells (10 and 20) are provided with covers (13 and 14) for holding the solution to allow the hydroxy substituted compounds to react with the film.

14 Claims, 3 Drawing Sheets

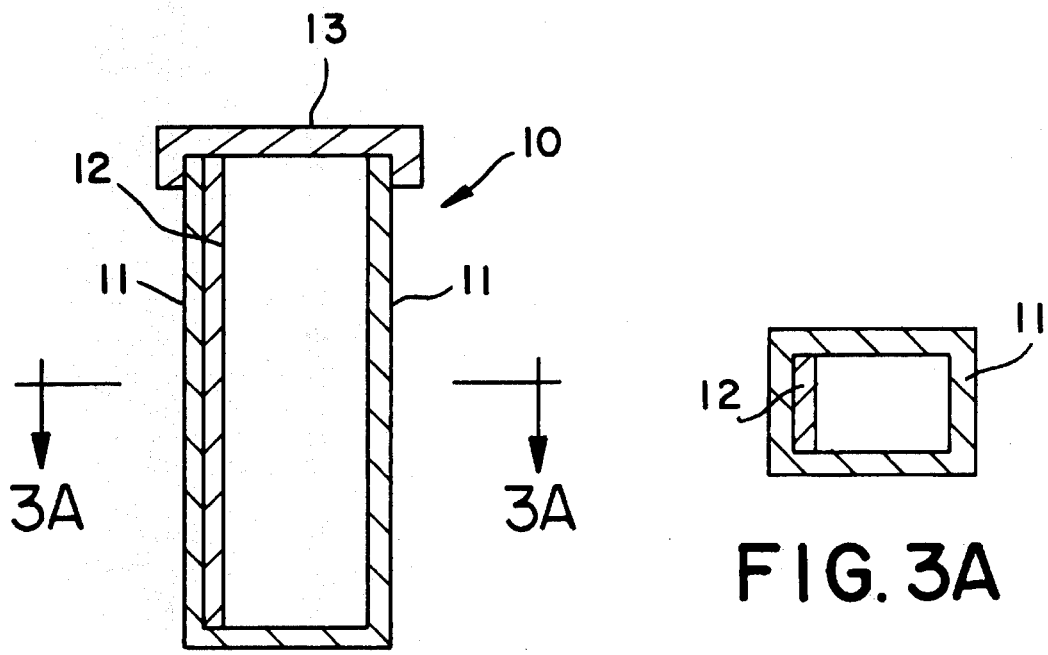
FIG. 3
FIG. 3A
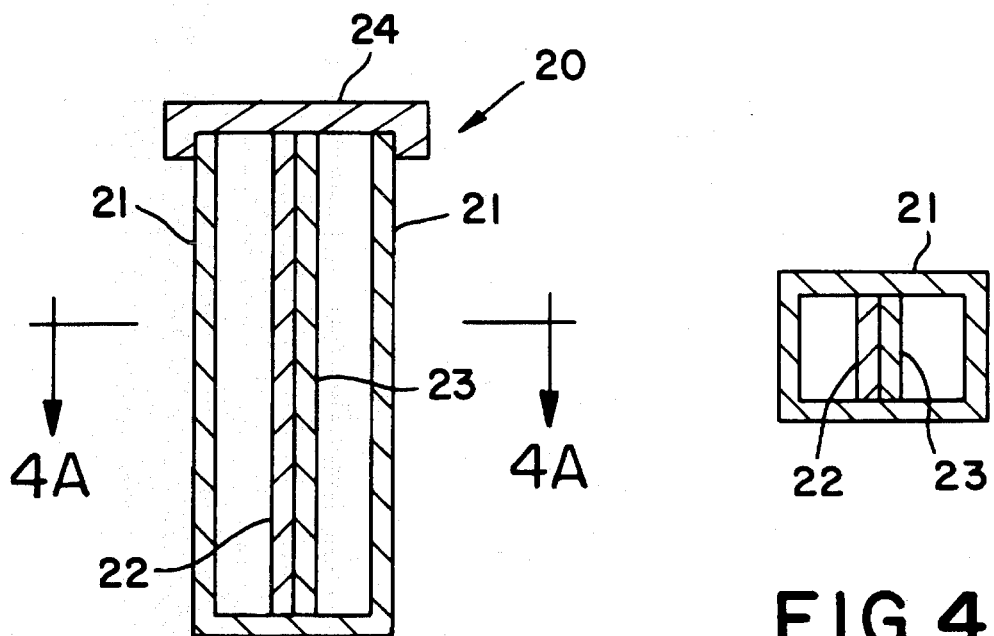
FIG. 4
FIG. 4A

METHOD FOR DETERMINING HYDROXY AROMATIC COMPOUNDS

BACKGROUND OF THE INVENTION

1. Field of the Invention

The present invention relates to a method and test kit for determining the presence of a hydroxy substituted aromatic compound in a solution using titanium films which change light absorbance in the presence of the compound. In particular, the present invention relates to the use of preferred films prepared from a titanium alkoxide and an aliphatic carboxylic acid.

2. Prior Art

The polymerization of titanium alkoxide results from the hydrolysis of alkoxide groups as shown in equation (1).

Propagation occurs by subsequent polycondensation reactions. Two competitive mechanisms are possible during the polycondensation; they are olation and oxolation reactions. Olation is the formation of hydroxy bridges through the elimination of solvent molecules,

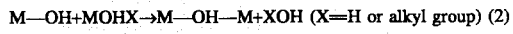

and, oxolation is the formation of oxygen bridges through the elimination of $H_2O$ or ROH,

These reactions result in the transformation of the titanium alkoxide into the titanium oxide network. The contribution of each reaction determines the structure and morphology of the titanium oxide network.

The reaction of carboxylic acid with titanium alkoxide has been used to prepare titanium alkoxide precursors (Sanchez, C., et al., J. Non-Cryst. Solids 100, 65 (1988); Sanchez, C., et al., New J. Chem. 14, 513 (1990); and Sanchez, C., et al., in "Ultrastructure Processing of Advance Ceramics", Mackenzie, J. D.,; Ulrich, D. R. Eds, Wiley, N.Y. P. 77 (1988)). Changes in the titanium alkoxide precursors modify the hydrolysis and polycondensation reactions of the titanium alkoxide (Doeuff, S., et al., J. Non-Cryst. Solids 89, 206 (1987)). There are several U.S. patents on the preparation of polymeric titanium complexes with carboxylic acids (U.S. Pat. No. 2,621,193 (Dec. 9, 1952) to Langkammerer; U.S. Pat. No. 2,621,194 (Dec. 9, 1952; and U.S. Pat. No. 2,621,195 (Dec. 9, 1952) to Haslam). Titanium oxide gels (Gagliardi, C. D., et al., Mat. Res. Soc. Symp. Proc., 155, 127 (1989); and Livage, J., Mat. Res. Soc. Symp. Proc. 73, 717 (1986)) and films (Gagliardi, C. D., et al., Mat. Res. Soc. Symp. Proc., 180, 801 (1990)) have also been prepared by the controlled hydrolysis of the titanium alkoxide carboxylic acid precursors. The actual titanium oxide network has not been fully characterized. It is possible that the titanium oxide network may still undergo further reactions.

Color development is observed with titanium phenoxy complexes. For example dichlorodiphenoxytitanium (IV) (Watenpaugh, K., et al., Inorg. Chem. 5, 1782 (1966)) is red, tetraphenoxytitanium (IV) monophenolate ((a) Svetich, G. W., et al., J. Am. Chem. Soc. Chem. Commun., 676 (1971); (b) Svetich, G. W., et al., Acata Cryst. B28, 1760 (1972); and (c) Malhotra, K. C., et al., J. Organomet. Chem., 239, 159 (1982)) is an orange-red, isoproyltriphenoxy-titanium (IV) is a bright yellow (Varma, I. D., et al., J. Indian, Chem. Soc., 38, 147 (1961)), and $[NH_4]_2[Ti(catecholate)_3] \cdot 2H_2O^{14}$ is a rust color. U.S. Pat. No. 4,043,820 to Landau discloses using titanium-catechol chelate to develop color when applied as an ink to alkaline paper (U.S. Pat. No. 4,043,820 (Aug. 23, 1977) to Landau). Such complexations are well established in the liquid phase where coordination sites to the titanium IV are easily accessible but no such chelation has been reported when Ti(IV) ions are immobilized in a solid network.

There is a need for a simple, reliable method for the detection of phenolic compounds, particularly in the field when testing water sources for the presence of such contaminants. The prior art has used sophisticated instrumentation such as gas chromatograph or mass spectrograph for this purpose; however, the use of such instrumentation in the field produces unreliable results and is expensive.

OBJECTS

It is therefore an object of the present invention to provide a reliable and inexpensive method for the detection of hydroxy substituted aromatic compounds. Further, it is an object of the present invention to provide a method which can be easily adapted for use in the field. These and other objects will become increasingly apparent by those skilled in the art from the following description and the drawings.

BRIEF DESCRIPTION OF THE DRAWINGS

FIG. 3 is a front cross-sectional view showing a spectrophotometer cell 10 having a titanium film 12 deposited inside.

FIG. 3A is a cross-sectional view of FIG. 3 along line 3A—3A.

FIG. 4 is a front cross-sectional view of a spectrophotometer cell 20 showing a slide 22 with a titanium film 23 deposited thereon.

FIG. 4A is a cross-sectional view along line 4A—4A of FIG. 4.

GENERAL DESCRIPTION

Figure 1:
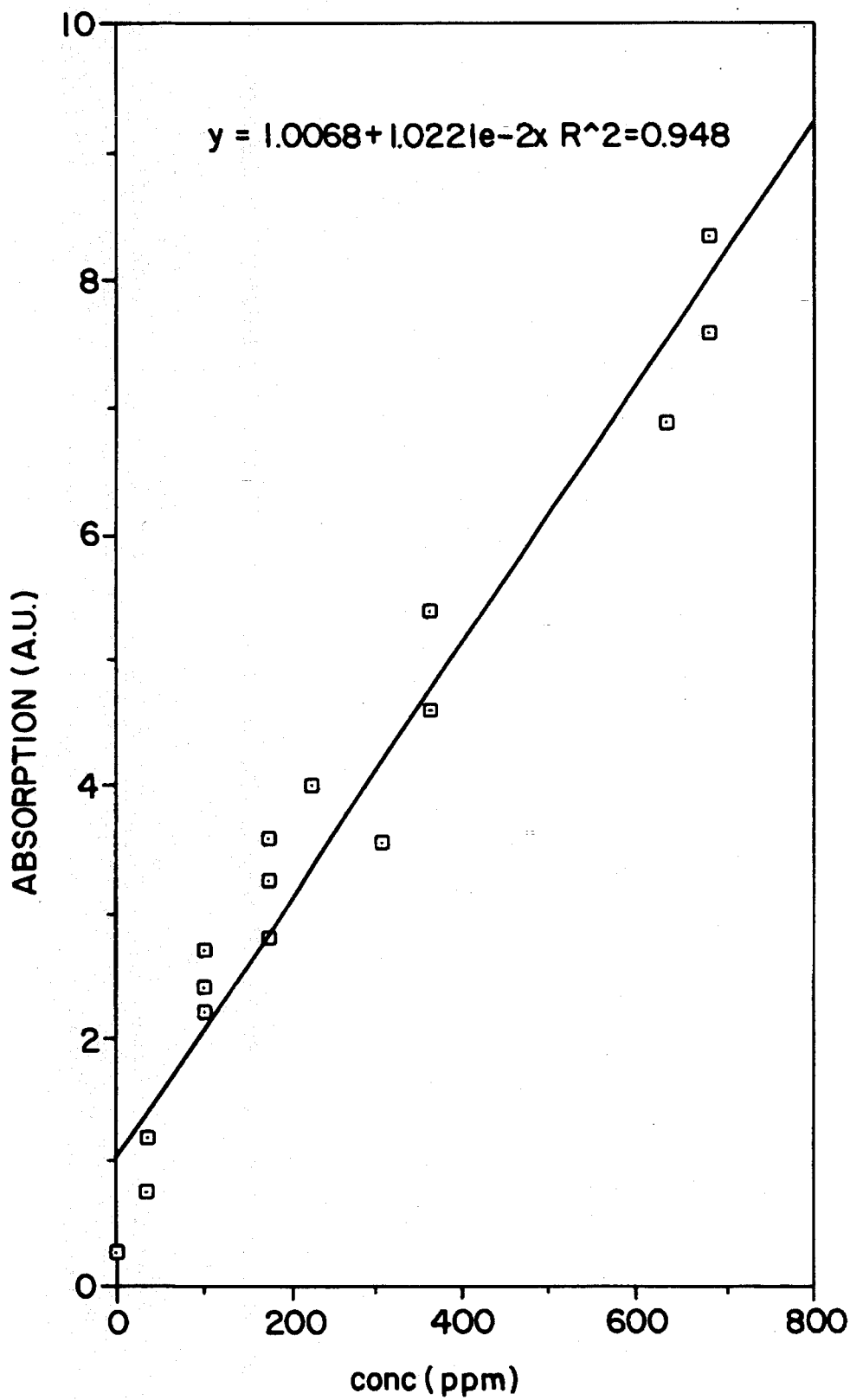
FIG. 1 is a graph showing a titanium film prepared as in Example 4 with the concentration as a function of absorbance for phenol solutions.
Figure 2:
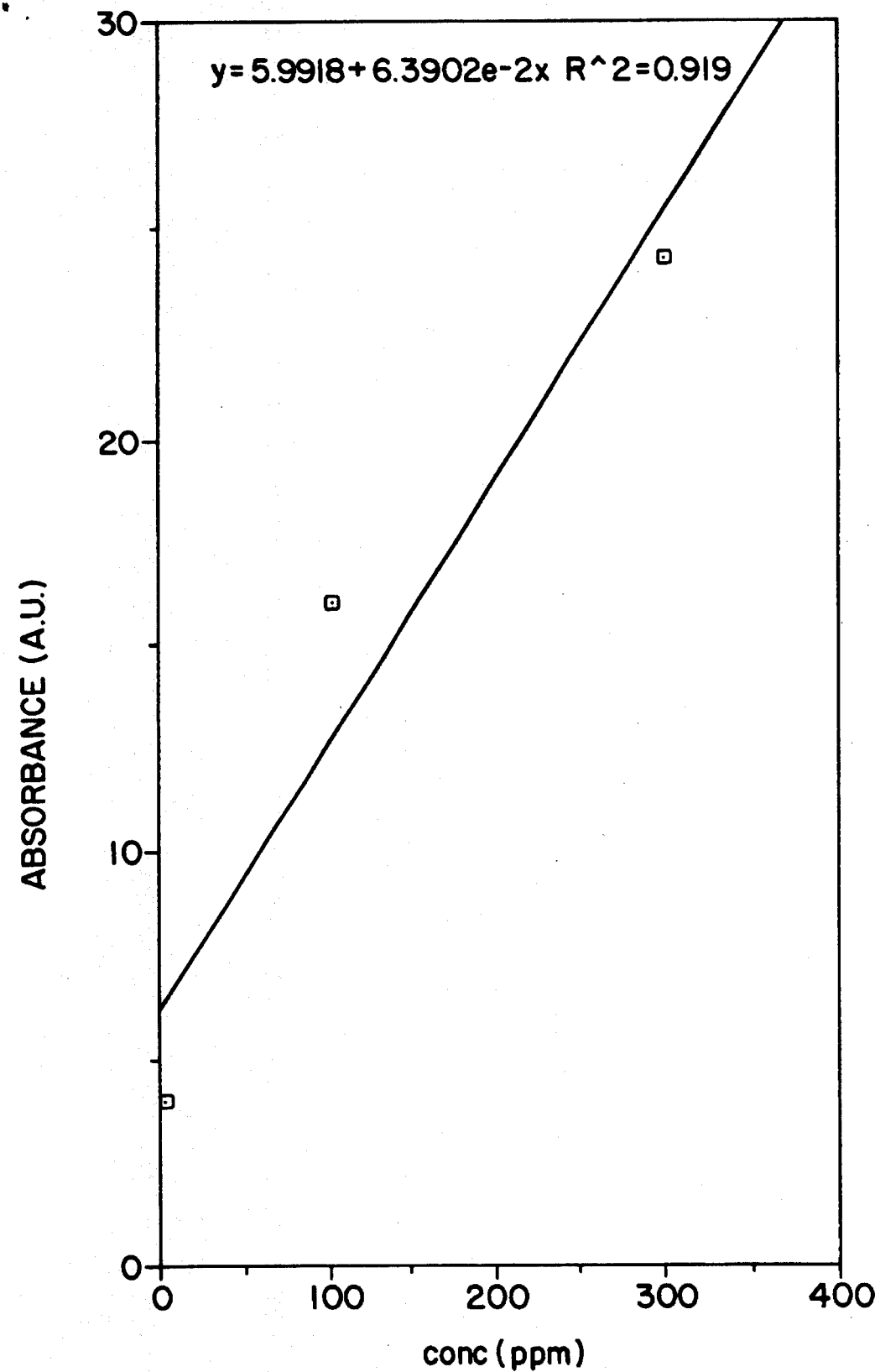
FIG. 2 is a graph showing a titanium film prepared as in Example 4 with the concentration as a function of absorbance for a pyrocatechol (1,2-dihydroxybenzene) solution.

The present invention relates to a method for determining the presence of a hydroxy substituted aromatic compound in a solution which comprises: providing a titanium film which changes light absorbance in the presence of the hydroxy substituted aromatic compound in solution; and contacting the film with the solution so as to determine the presence of the hydroxyaromatic compound because of a change of light absorbance of the film when the solution contains the hydroxy substituted aromatic compound.

The present invention also relates to a test kit for determining the presence of a hydroxy substituted aromatic compound in solution which comprises: a titanium film deposited on a transparent element which can be inserted in a spectrophotometer after contact with the solution. Preferably the transparent element is a sealable container which is openable for inserting the solution and, wherein the container is free of the aromatic compound.

The preferred titanium films are formed from the reaction of a titanium alkoxide and an aliphatic carboxylic acid. The alkoxide preferably contains 3 to 32 carbon atoms and the aliphatic carboxylic acid preferably contains between about 2 and 22 carbon atoms. The most preferred titanium alkoxide is titanium isopropoxide. The most preferred aliphatic carboxylic acids are valeric and lauric acids, alone or together. Usually the reaction is conducted in an aqueous solution.

Various hydroxy substituted aromatic compounds can be detected by the method and test kit of the present invention. Phenolic compounds like phenol, are readily detected. Other compounds which are detected are shown in the Examples.

Some compounds are not detected and it is believed that size and/or blocked or hindered hydroxy groups may be the reason for non-detection because the compounds do not react with the titanium film. Another possibility may be the development of complexes absorbing deeper into the ultraviolet region, therefore being undetectable to the eye and masked by the film absorption cutoff. The results are quantitative and reproducible.

Usually the detection is in a suspect aqueous solution since these are encountered in the field. The suspect aqueous solutions are tested using a spectrophotometer, preferably one operating in the visible to ultraviolet (UV) range. Such instruments are well known to those skilled in the art and can operate on the typical 12 volt system found in vehicles used in the field. If necessary an auxiliary generator can be used if a higher voltage is necessary. Hand-held, battery operated spectrophotometers are also suitable.

As shown in FIGS. 3 and 3A the transparent element can be a spectrophotometer cell 10 coated with the film 12. The cell 10 has a container portion 11 and a cover 13. The cell 10 can be disposed of or recycled by removing the old film 12 and depositing a new film. Silica glass can be used to make the cell 10. As shown in FIGS. 4 and 4A, a cell 20 can also be used with a container portion 21 and cover 24 and a slide 22 coated with the titanium film 23. The slide 22 is of the type used with optical microscopes.

SPECIFIC DESCRIPTION

In the examples below, the titanium films change from a colorless transparent film to a yellow or orange color depending on the type and the concentration of a phenolic compound (hydroxybenzene compound) present in aqueous solutions brought in contact with the film. This is because of the change in absorbance of the film in the presence of the phenolic compound. When these titanium films are soaked in 100 ppm aqueous pyrocatechol (1,2-dihydroxybenzene) solutions the titanium films turn to an orange color.
(1) Preparation of the Titanium Films In the examples that follow the titanium alkoxide carboxylate films produced are referred to as "titanium films".

Example 1

Titanium film I: Valeric acid (1.6 ml, $1.52 \times 10^{-2}$ moles) was added to titanium isopropoxide (0.50 ml, $1.63 \times 10^{-3}$ moles) the solution was mixed, water (42 L, $2.33 \times 10^{-3}$ mole) was added, and the solution was stirred again.

Example 2

Titanium film II: Valeric acid (2.7 ml, $2.48 \times 10^{-2}$ moles) was added to titanium isopropoxide (1.00 ml, $3.26 \times 10^{-3}$ moles) the solution was mixed, water (0.61 mL, $3.39 \times 10^{-2}$ mole) was added, and the solution was stirred again.

Example 3

Titanium film III: Valeric acid (1.6 ml, $1.52 \times 10^{-2}$ moles) was added to titanium isopropoxide (0.5 ml, $1.63 \times 10^{-3}$ moles) the solution was mixed, and then water (0.30 mL, $1.67 \times 10^{-2}$ mole) was added, and the solution was stirred again.

Example 4

Titanium film IV: Lauric acid (0.250 gm, $1.25 \times 10^{-3}$ mole) was added to titanium isopropoxide (1.00 ml, $3.26 \times 10^{-3}$ mole). The mixture was heated with a hot air gun until all of the lauric acid dissolved. Valeric acid (2.50 ml, $2.30 \times 10^{-2}$ moles) was added to the hot solution. The solution was stirred and an exothermic reaction took place. Water (92 µL, $5.11 \times 10^{-3}$ mole) was then added, and the solution was stirred.

Example 5

Titanium film V: Lauric acid (0.250 gm, $1.25 \times 10^{-3}$ mole) was added to titanium isopropoxide (1.00 ml, $3.26 \times 10^{-3}$ mole). The mixture was healed with a hot air gun until all of the lauric acid dissolved. Valeric acid (2.50 ml, $2.30 \times 10^{-2}$ moles) was added to the hot solution. The solution was stirred and an exothermic reaction took place. Water (0.61 ml, $3.39 \times 10^{-2}$ mole) was then added, and the solution was stirred.

Example 6

Titanium film VI: Lauric acid (0.250 gm, $1.25 \times 10^{-3}$ mole) was added to titanium isoproproxide (1.00 ml, $3.26 \times 10^{-3}$ mole). The lauric acid was dissolved by placing the mixture in a sonic bath for 2 minutes. Valeric acid (2.50 ml, $2.30 \times 10^{-2}$ moles) was added and the solution was stirred. Water (0.61 mL, $3.39 \times 10^{-2}$ mole) was then added, and the solution was stirred.

Example 7

Titanium film VII: Lauric acid (0.250 gm, $1.2 \times 10^{-3}$ mole) was added to titanium isopropoxide (1.00 ml, $3.26 \times 10^{-3}$ mole). The mixture was heated with a hot air gun until all of the lauric acid dissolved. Valeric acid (2.50 ml, $2.30 \times 10^{-2}$ moles) was added to the hot solution. The solution was stirred and an exothermic reaction took place. TMOS (tetramethyl ortho silicon, 1.0 mL, $6.65 \times 10^{4}$ moles) was added and stirred into the reaction mixture. Water (0.61 mL, $3.39 \times 10^{-2}$ mole) was then added and the reaction mixture was stirred.

Example 8

Titanium film VIII: Lauric acid (0.250 gm, $1.25 \times 10^{-3}$ mole) was added to titanium isopropoxide (1.00 ml, $3.26 \times 10^{-3}$ mole). The mixture was heated with a hot air gun until all of the lauric acid dissolved. Valeric acid (2.50 ml, $2.30 \times 10^{-2}$ moles) was added to the hot solution. The solution was stirred and an exothermic reaction took place. Dow Corning Z-6020 (N-(β-aminoethyl)-γ-aminopropyltrimethysilane) (0.3 mL, $1.38 \times 10^{-3}$ moles) was added and stirred into the reaction mixture. Water (0.61 mL, $3.39 \times 10^{-2}$ moles) was then added and the reaction mixture was stirred.
(2) Film Formation and Instrumentation The titanium films were prepared from the polymers of Examples 1 to 8 by spin casting 60 µL of the film solution on a 50 mm×8 mm silica slide. The titanium film is placed in a quartz cell, and the film was first soaked in water, for 10 minutes, then the water was removed and the phenolic solution was placed in the cell. A Perkin-Elmer Lambda 3A UV/Vis Spectrophotometer was used to record the electronic absorption spectra.

(a) When the titanium film I was soaked in water the film turned to a very light yellow. If the film was exposed to air for several days the titanium film also turned to a very light yellow. The titanium film was soaked for 2 hours in 112 ppm catechol and the absorbance maximum was 0.178 at 350 nm (the titanium film was 6 days old).

(b) When the titanium film II was soaked in water the film turned to a very light yellow. If the film is exposed to air for several days the titanium film also turns to a very light yellow. The titanium film was soaked in 112 ppm catechol for 2 hours and the absorbance maximum was 0.260 at 350 nm.

(c) When the titanium film IV was soaked in water a very light yellow color in the titanium film was noticed if the film was placed next to a titanium film made from Example II. The titanium film IV was soaked in 105 ppm catechol for two hours and the absorption maximum was 0.315 at 350 nm.

The following compounds result in color changes when contacted with the titanium film IV. Phenol, 1-naphthol, 3,5-dihydroxybenzoic acid, catechol (1,2-dihydroxybenzene), resorcinol (1,3-dihydroxybenzene), pyrogallol (1,2,3-trihydroxybenzene), phloroglucinol (1,3,5-trihydroxybenzene), anisole. Others that react are orcinol, chrysin, esculetin 7-hydroxy- 4-methyl coumarin. Phenolic complexes that have two hydroxyl groups in the 1,2 position (catechol, and pyrogallol) appeared to interact more readily with the titanium film, and yield more intense absorbance bands. For similar concentrations of catechol and pyrogallol, soaking the titanium films the same amount of time resulted in similar intensities of the absorption. The intensity of catechol and pyrogallol absorption bands were approximately 8 times greater than that of phenol, resorcinol, hydroquinone, and phloroglucinol absorptions. The lowest detection of catechol was 305 ppb ($2.77 \times 10^{-6}$M), and for phenol it was 32.6 ppm ($3.46 \times 10^{-4}$M).

The following is a list of compounds that do not result in color changes when contacted with the titanium film IV: aniline, benzaldehyde, benzene, unsaturated alcohols, disodium L-tyrosine, benzyl alcohol, 4-amino-3,5,6-trichloropicolinic sodium salt, pyranine, heptafluorobutyric acid, aluminum nitrate, BHT, 4,5-dihydroxynaphthalene-2,7-disulfonic acid (disodium salt) Acac, EDTA, 1,10-phenanthroline, 2,5-dichloro 3,6-dihydroxyl-p-benzoquinone (chloranilic acid), tetrachloro-1,2-benzoquinone (o-chloronil) juglone, lawsone, veratrole, sorbitol, dopamine, 1,2-naphthoquinone, phloretin. 1,2,4-Trihydroxybenzene dissolved in water produced a pink solution, and the titanium film turned pink.

(e) When the titanium film V was soaked in water there was no color change in the film. The titanium film was soaked in 116 ppm catechol for 2 hours the absorbance maximum was 0.313 at 350 nm.

(f) When the titanium film VI was soaked in water there was no color change in the film. The titanium film was soaked in 116 ppm catechol for 2 hours the absorbance maximum was 0.360 at 350 nm.

(g) The mixed titanium silicon film was placed in a catechol solution and the film turned yellow-brown.

(h) The mixed titanium silicon film VIII film was stable in water, but turns cloudy white when placed in methanol.

It is intended that the foregoing description and Examples be only illustrative of the present invention and that the present invention be limited only by the hereinafter appended claims.

We claim

1. A method for determining the presence of a hydroxy substituted aromatic compound in a solution which comprises:

(a) providing a titanium containing film formed from a reaction of a titanium alkoxide and an aliphatic carboxylic acid which changes light absorbance in the presence of the hydroxy substituted aromatic compound in solution; and (b) determining the presence of the hydroxy aromatic compound because of a change of light absorbance of the film in contact with the solution when the solution contains the hydroxy substituted aromatic compound.

2. The method of claim 1 wherein the titanium alkoxide contains between 3 and 32 carbon atoms.

3. The method of claim 1 wherein the titanium alkoxide is titanium isopropoxide.

4. The method of claim 1 wherein the aliphatic carboxylic acid is an alkyl carboxylic acid containing between about 2 and 22 carbon atoms.

5. The method of claim 1 wherein the aliphatic carboxylic acid is valeric acid.

6. The method of claim 1 wherein the acid is lauric acid.

7. The method of claim 1 wherein the titanium alkoxide is titanium isopropoxide and the aliphatic carboxylic acid is valeric acid.

8. The method of claim 1 wherein the change of light absorbance is directly proportional to a quantity of the hydroxy substituted aromatic compound.

9. The method of claim 1 wherein the hydroxy substituted aromatic compound is a phenolic compound.

10. The method of claim 1 wherein the solution is an aqueous solution and wherein the method quantitatively determines the hydroxy substituted compound.

11. The method of claim 1 wherein the film is tested with a spectrophotometer to determine the change in light absorbance of the film after exposure to the hydroxy substituted aromatic compound.

12. The method of claim 11 wherein the film is supported on a transparent surface for determining the absorbance.

13. The method of claim 12 wherein the transparent surface is a silica glass microscope slide.

14. The method of claim 13 wherein the slide is mounted in a quartz cell containing an aqueous solution containing the hydroxy substituted aromatic compound which is then tested with the spectrophotometer to determine the absorbance.

* * * * *